United States Patent
Boas et al.

(10) Patent No.: US 11,660,010 B2
(45) Date of Patent: May 30, 2023

(54) SYSTEMS AND METHODS FOR PATH LENGTH SELECTED DIFFUSE CORRELATION SPECTROSCOPY

(71) Applicant: The General Hospital Corporation, Boston, MA (US)

(72) Inventors: David Boas, Winchester, MA (US); Jason Sutin, Cambridge, MA (US); Maria Angela Franceschini, Winchester, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 17/508,718

(22) Filed: Oct. 22, 2021

(65) Prior Publication Data

US 2022/0248971 A1 Aug. 11, 2022

Related U.S. Application Data

(63) Continuation of application No. 16/079,881, filed as application No. PCT/US2017/019533 on Feb. 24, 2017, now abandoned.
(Continued)

(51) Int. Cl.
*A61B 5/026* (2006.01)
*A61B 5/00* (2006.01)
*A61B 5/1455* (2006.01)

(52) U.S. Cl.
CPC .......... *A61B 5/0261* (2013.01); *A61B 5/0075* (2013.01); *A61B 5/14552* (2013.01);
(Continued)

(58) Field of Classification Search
CPC ... A61B 5/261; A61B 5/0075; A61B 5/14552; A61B 5/4064; A61B 5/14551;
(Continued)

(56) References Cited

U.S. PATENT DOCUMENTS

2009/0268020 A1  10/2009  Buckland et al.
2010/0056927 A1  3/2010   Van Gogh et al.
(Continued)

FOREIGN PATENT DOCUMENTS

WO  2013090658 A1  6/2013
WO  2015109005 A1  7/2015
(Continued)

OTHER PUBLICATIONS

Sutin, Jason, Bernhard Zimmerman, Danil Tyulmankov, Davide Tamborini, Kuan Cheng Wu, Juliette Selb, Angelo Gulinatti et al. "Time-domain diffuse correlation spectroscopy." Optica 3, No. 9 (2016): 1006-1013.*
(Continued)

*Primary Examiner* — Carolyn A Pehlke
(74) *Attorney, Agent, or Firm* — Quarles & Brady LLP

(57) ABSTRACT

Systems and methods for path length selected diffuse correlation spectroscopy (PLS-DCS) are disclosed. The systems and methods are suitable for measuring dynamics of a target medium. The systems and methods can utilize light sources having a coherence length that is shorter than a path length distribution of the target medium and can utilize a reference optical path to interferometrically detect PLS-DCS signals. The coherence length and reference path length can be selected to provide sensitivity to portions of the target medium that correspond to a desired path length distribution.

7 Claims, 7 Drawing Sheets

Related U.S. Application Data

(60) Provisional application No. 62/299,080, filed on Feb. 24, 2016.

(52) U.S. Cl.
CPC ........ *A61B 5/4064* (2013.01); *A61B 5/14551* (2013.01); *A61B 5/14553* (2013.01); *A61B 5/6814* (2013.01); *A61B 2562/0238* (2013.01); *A61B 2562/0242* (2013.01)

(58) Field of Classification Search
CPC .............. A61B 5/14553; A61B 5/6814; A61B 2562/0238; A61B 2562/0242
See application file for complete search history.

(56) References Cited

U.S. PATENT DOCUMENTS

| | | |
|---|---|---|
| 2010/0168586 A1 | 7/2010 | Hillman et al. |
| 2013/0187649 A1 | 7/2013 | Bhat et al. |
| 2014/0052006 A1 | 2/2014 | Lee et al. |
| 2016/0360967 A1* | 12/2016 | Nishiwaki ............. G01J 1/0422 |
| 2017/0284789 A1* | 10/2017 | Nishiwaki ............... H01L 31/00 |
| 2018/0164160 A1* | 6/2018 | Nishiwaki .......... G01B 9/02087 |

FOREIGN PATENT DOCUMENTS

| | | |
|---|---|---|
| WO | 2015127309 A1 | 8/2015 |
| WO | 2015134245 A1 | 9/2015 |

OTHER PUBLICATIONS

PCT International Search Report and Written Opinion, PCT/US2017/019533, dated Jun. 12, 2017, 15 pages.

Borycki, et al., "Interferometric Near-Infrared Spectroscopy (iNIRS) for determination of optical and dynamical properties of turbid media." Optics express 24, No. 1 (2016): 329-354.

Sutin, et al., "Tim-domain diffuse correlation spectroscopy." Optica 3, No. 9 (2016): 1006-1013.

\* cited by examiner

SYSTEMS AND METHODS FOR PATH LENGTH SELECTED DIFFUSE CORRELATION SPECTROSCOPY

CROSS-REFERENCE TO RELATED APPLICATIONS

This application is a continuation of U.S. application Ser. No. 16/079,881 filed on Aug. 24, 2018 which is a U.S. National Phase of PCT/US2017/019533 filed on Feb. 24, 2017 which is related to, claims priority to, and incorporates herein by reference for all purposes U.S. Provisional Patent Application No. 62/299,080, filed Feb. 24, 2016.

STATEMENT REGARDING FEDERALLY SPONSORED RESEARCH

This invention was made with government support under P41-EB015896, R01-HD042908, and R01-EB001954 awarded by the National Institutes of Health. The government has certain rights in the invention.

BACKGROUND

Diffuse correlation spectroscopy (DCS) is a method which can be used to measure blood flow non-invasively in buried tissues such as the brain from a sensor on the surface of the body. In the prior art, for DCS a small region of the body is illuminated with a long coherence length light source and the light is detected by a detector after it traverses through the body. The blood flow signal is represented by changes in the intensity autocorrelation of the detected light.

A difficulty with DCS measurements is that the total signal consists of both unwanted signals from the intervening superficial tissues along with the desired signals from the tissues of interest. For example, when non-invasively measuring brain blood flow by DCS, the flow signal is dominated by unwanted flow signals for the scalp with only a minority of the detected signal consisting of the desired signals from the brain. This problem occurs because in the prior art, DCS detects all light from the source which reaches the sensor regardless of the path it took through the tissue.

There exists a need for new and improved systems and methods for measurement of fluid flow, and specifically, non-invasive measurement of blood flow.

SUMMARY

The present disclosure overcomes drawbacks of previous technologies by providing systems and methods for path length selected diffuse correlation spectroscopy (PLS-DCS).

In an aspect, the present disclosure provides a PLS-DCS system. The PLS-DCS system can include a reference optical path, a PLS-DCS source, a PLS-DCS detector, a memory, and a processor. The PLS-DCS source can be configured to emit a first light having a coherence length of between 0.01 mm and 3000 mm. The PLS-DCS source can be configured to transmit a first portion of the first light into a target medium and a second portion of the first light along the reference optical path. The PLS-DCS detector can be configured to receive at least part of the first portion of the first light from the target medium and at least part of the second portion of first light from the reference optical path. The PLS-DCS detector can be configured to generate a PLS-DCS detector signal in response to receiving the first portion of light and the second portion of light. The PLS-DCS detector can be configured for interferometric detection. The memory can have stored thereon one or more equations relating correlation to dynamics of scattering particles within the target medium. The processor can be coupled to the PLS-DCS detector and the memory. The processor can be configured to determine a dynamics of the target medium using the PLS-DCS detector signal and the one or more equations.

In another aspect, the present disclosure provides a method for making a PLS-DCS measurement of scattering particle dynamics within a target medium. The method can include the following steps: a) coupling a PLS-DCS source and a PLS-DCS detector to the target medium, the PLS-DCS source configured to emit a first light having a first coherence length of less than a path length distribution of the target medium; b) selecting the first coherence length of the first light and/or a first path length of a first reference optical path to acquire a PLS-DCS measurement for a desired path length distribution of the target medium; c) transmitting a first portion the first light from the PLS-DCS source into the target medium and a second portion of the first light along the first reference optical path; d) combining at least a portion of the first portion of the first light after passing through the target medium and the second portion of the first light after passing along the first path length of the first reference optical path, thereby providing a combined optical signal; e) receiving the combined optical signal at the PLS-DCS detector, thereby generating a PLS-DCS detector signal including path length information and correlation information for the combined optical signal; f) determining, using a processor, the path length information, the correlation information, and one or more equations relating path length and correlation to dynamics, a dynamics of the target medium; and g) generating a report including the dynamics of the target medium.

In yet another aspect, the present disclosure provides a method of making a PLS-DCS measurement of a target medium. The method can include the following steps: a) coupling a PLS-DCS source and a PLS-DCS detector to a surface of the target medium; b) transmitting a first portion of a first light from the PLS-DCS source into the target medium and a second portion of the first light along a reference optical path, the first light having a first coherence length of less than a path length distribution of the target medium; c) interferometrically detecting, using the PLS-DCS detector, at least a portion of the first portion of the first light after passing through the medium and the second portion of the first light after passing along a first path length of the reference optical path, thereby generating a first interferometric signal; d) repeating steps b) and c), substituting a second coherence length for the first coherence length and a second path length for the first path length, thereby generating a second interferometric signal in place of the first interferometric signal, wherein the second coherence length is different than the first coherence length or the second path length is different than the first path length; e) determining a first measured path length distribution based on the first coherence length and the first path length and a second measured path length distribution based on the second coherence length and the second path length; f) determining, using a longer distribution between the first measured path length distribution and the second measured path length distribution, an inner dynamics of an inner portion of the target medium relative to the surface, or, using a shorter distribution between the first measured path length distribution and the second measured path length distribution, a superficial dynamics of a superficial layer of the target medium relative to the surface; and g) generating a report including the inner dynamics or the superficial dynamics.

The foregoing and other advantages of the disclosure will appear from the following description. In the description, reference is made to the accompanying drawings which form a part hereof, and in which there is shown by way of illustration a preferred embodiment of the disclosure. Such embodiment does not necessarily represent the full scope of the disclosure, however, and reference is made therefore to the claims and herein for interpreting the scope of the disclosure.

BRIEF DESCRIPTION OF THE DRAWINGS

The present disclosure will hereafter be described with reference to the accompanying drawings, wherein like reference numerals denote like elements.

DETAILED DESCRIPTION

Figure 1:
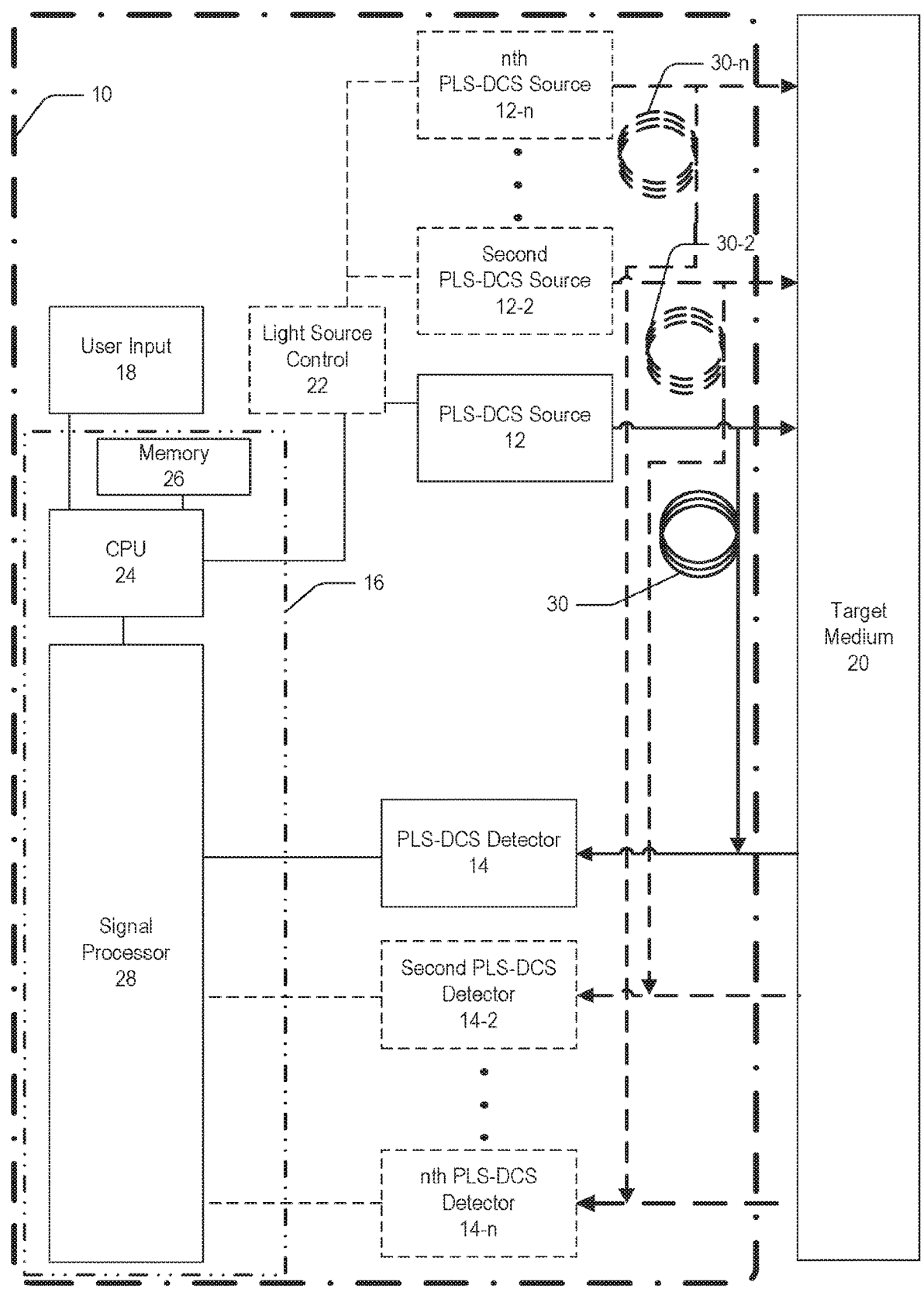
FIG. 1 is a schematic of a system, in accordance with the present disclosure.

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising", "including", or "having" should be interpreted as referring to elements, components, or steps in a non-exclusive manner, so the referenced elements, components, or steps may be combined with other elements, components, or steps that are not expressly referenced. Embodiments referenced as "comprising", "including", or "having" certain elements are also contemplated as "consisting essentially of" and "consisting of" those elements, unless the context clearly dictates otherwise. It should be appreciated that aspects of the disclosure that are described with respect to a system are applicable to the methods, and vice versa, unless the context explicitly dictates otherwise.

Numeric ranges disclosed herein are inclusive, so recitation of a value of between 1 and 10 includes the values 1 and 10. Disclosure of multiple alternative ranges having different maximum and/or minimum values contemplates all combinations of the maximum and minimum values disclosed therein. For example, recitation of a value of between 1 and 10 or between 2 and 9 contemplates a value of between 1 and 9 or between 2 and 10 in addition to the positively recited values, unless explicitly stated to the contrary.

This disclosure provides systems and methods for path length selected diffuse correlation spectroscopy (PLS-DCS).

As used herein, the terms "time of flight" and "path length" are used interchangeably to refer to the length of time and/or the distance that a photon travels from the source to detector.

As used herein, the terms "timing" and "phase shift" are used interchangeably to refer to the relative timing of coherent light sources.

Systems

Referring to FIGS. 1, 2, 3, and 4, a system 10, 110, 210, 310 suitable for executing the methods of the present disclosure is provided. The system 10, 110, 210, 310 can include a PLS-DCS source 12, 112, 212, 312 and a PLS-DCS detector 14, 114, 214, 314. The system 10 can include a computer 16, 116, 216, 316 in electronic communication with the PLS-DCS source 12, 112, 212, 312 and the PLS-DCS detector 14, 114, 214, 314. The system 10, 110, 210, 310 can also include a user input 18, 118, 218, 318 configured to provide an interface between a user and the computer 16, 116, 216, 316 and/or other aspects of the system 10, 110, 210, 310 (connections between the user input 18, 118, 218, 318 and the other aspects are not illustrated, but can be appreciated by a person having ordinary skill in the art). The system 10, 110, 210, 310 can include a reference optical path 30, 130, 230, 330. The PLS-DCS source 12, 112, 212, 312 and the PLS-DCS detector 14, 114, 214, 314 can be coupled to a target medium 20, 120, 220, 320. The system 10, 110, 210, 310 can include one or more beamsplitters (not pictured) to provide a first portion of light emitted from the PLS-DCS source 12, 112, 212, 312 to transmit into the target medium 20, 120, 220, 320 and a second portion of the light emitted from the PLS-DCS source 12, 112, 212, 312 to transmit along the reference optical path 30, 130, 230, 330.

Figure 5:
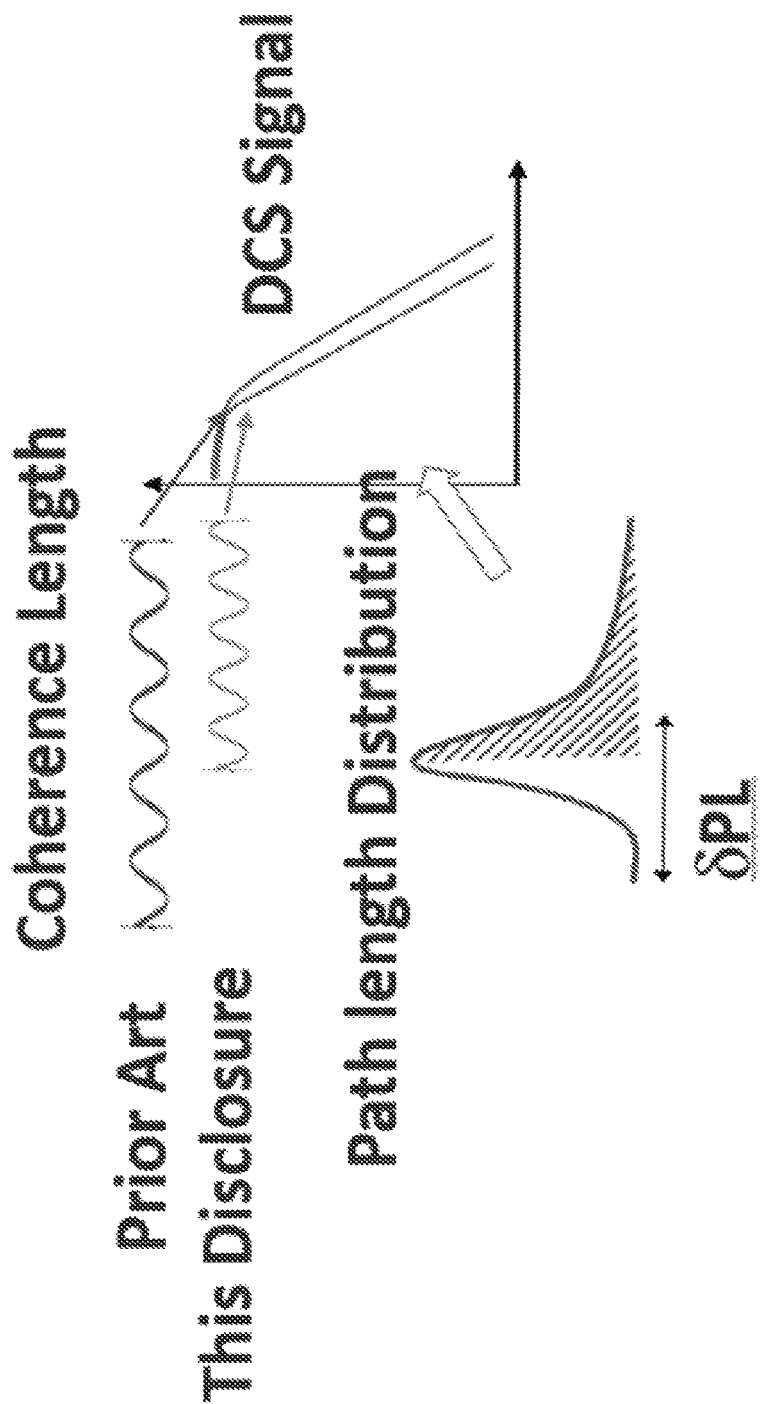
FIG. 5 is an illustration comparing prior art diffuse correlation spectroscopy principles with the principles of the present disclosure.

Referring to FIG. 5, a primary difference between systems of the prior art and the present disclosure is illustrated. In the prior art, the coherence length is longer than the coherence length contemplated for the present disclosure. The path length distribution illustrated would be fully covered by the coherence length used in the prior art, but the shorter coherence length of the present disclosure covers only a portion of the pathlength distribution. In the illustrated aspect, the length of the variable path length (δPL) is selected to provide sensitivity to the longer half of the path length distribution. The DCS signal from the prior art is sensitive to all achievable path lengths, whereas the DCS signal from the present disclosure is sensitive only to the longer path lengths.

In some cases, the systems and methods disclosed herein can be used to measure short path length signals and intermediate path length signals, as well as the longer path length signals described above. In these cases, some sources and/or detectors can be dedicated to measuring short path lengths, whereas others can be dedicated to measuring longer path lengths. This feature allows superficial signals to be measured along with deeper signals, and allows the results from the superficial signals to regress out residual superficial contributions to the deeper signals, thus improving sensitivity to the deeper dynamics.

Systems and methods are provided to select the DCS signal of interest interferometrically according to optical path length through the tissue. By selecting different distributions of path lengths, the measured DCS signal consists of different amounts of contributions from the various tissues sampled along the optical path. For example, in brain measurement, by selecting light which has travelled long path lengths, the light has traveled predominately through the brain and less in the scalp. The resulting DCS signals correspondingly predominately consist of the desired flow signal from the brain and less of the unwanted signal from the scalp. Similar results hold for other types of tissue measurements.

In the prior art it was assumed the coherence length of the light source must be as long as or longer than the longest path length through the tissue from the light source to the detector. Shorter coherence light was assumed to be unsuitable for DCS measurements because the coherence factor is reduced with a corresponding reduction the signal to noise ratio. In this disclosure, utilization of shorter coherence illumination is found to have an unexpected benefit of enabling discrimination of optical path lengths and a corresponding discrimination of the contribution of dynamic flow signals from different tissues.

In this disclosure, the illumination coherence length is not chosen to be longer than the entire path length as in the prior art, but is chosen to be shorter, only of length of a smaller desired fraction of the path length distribution. In this way, it becomes possible to select the autocorrelation signal only from the fraction of light with the desired path lengths. For example, for non-invasive measurement of the brain, the coherence length could be chosen to be small fraction of the path length distribution. Interferometery is then employed to select which portion of the path length is selected, such that the interference occurs around the path length difference between the arms of the interferometer in a distribution of length determined by the coherence profile of the source illumination.

The PLS-DCS source 12, 112, 212, 312 can be a light source that is capable of emitting optical signals having the properties described elsewhere in the present disclosure. The PLS-DCS source 12, 112, 212, 312 can be a single-mode laser, a multi-mode laser, combinations thereof, and the like. The PLS-DCS source 12, 112, 212, 312 can be a diode laser, a solid-state laser, a fiber laser, a vertical cavity surface-emitting laser (VCSEL), a Fabry-Perot laser, a ridge laser, a ridge waveguide laser, a tapered laser, a master oscillator power amplifier (MOPA) laser, or other type of laser.

The PLS-DCS source 12, 112, 212, 312 can be configured to transmit light into the target medium 20, 120, 220, 320 having a wavelength of between 400 nm and 1500 nm, including but not limited to, a wavelength of between 600 nm and 1000 nm, a wavelength of between 690 nm and 900 nm, a wavelength of between 450 nm and 750 nm, a wavelength of between 500 nm and 1250 nm, a wavelength of between 800 nm and 1350 nm, a wavelength of between 1000 nm and 1400 nm, or a wavelength of between 750 nm and 1450 nm. The PLS-DCS source 12, 112, 212, 312 can be configured to transmit light into the target medium 20, 120, 220, 320 having an average power of between 10 μW and 10 W, including but not limited to, an average power of between 100 μW and 1 W, between 1 mW and 500 mW, or between 10 mW and 200 mW.

The PLS-DCS source 12, 112, 212, 312 can be configured to transmit light into the target medium 20, 120, 220, 320 having a coherence length that is of the same order of magnitude as the path length distribution width of the light travelling through the target medium 20, 120, 220, 320. The PLS-DCS source 12, 112, 212, 312 can be configured to transmit pulses of light into the target medium 20, 120, 220, 320 having a coherence length of between 0.01 mm and the path length distribution width, including but not limited to, a coherence length of between 0.3 mm and 3000 mm, between 3 mm and 300 mm, between 15 mm and 210 mm, or between 30 mm and 150 mm.

In certain cases, the PLS-DCS source 12, 112, 212, 312 can have an adjustable coherence length, thus allowing tuning of the coherence length for desired applications. For example, the coherence length can be tuned by adjusting the current in a vertical cavity surface-emitting laser (VCSEL). As another example, the coherence length can be tuned by pulsing a laser.

Figure 2:
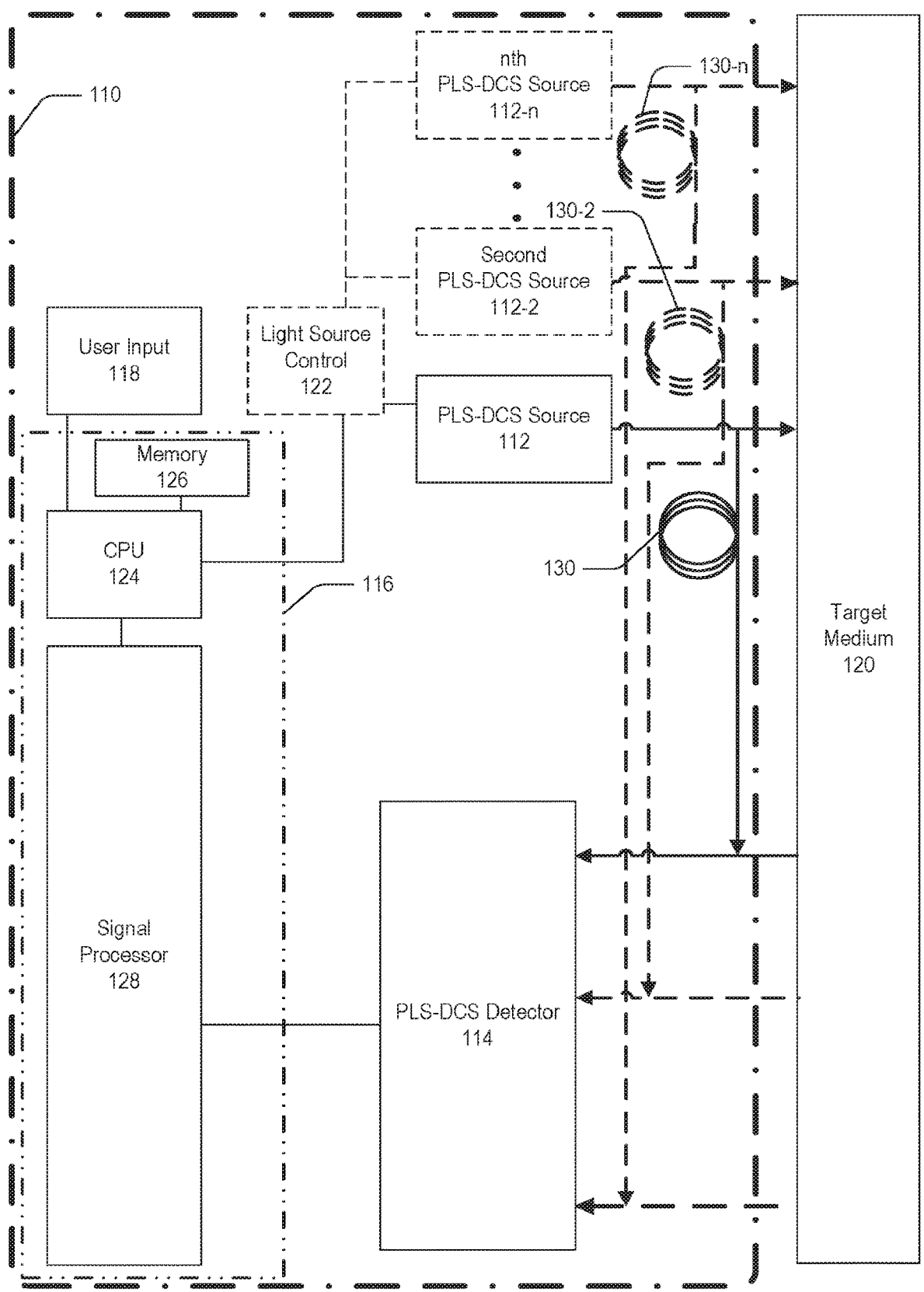
FIG. 2 is a schematic of a system, in accordance with the present disclosure.

Referring to FIGS. 1 and 2, in certain aspects, the system 10, 110 can further optionally include a second PLS-DCS source 12-2, 112-2. The system 10, 110 can also optionally include a third PLS-DCS source, a fourth PLS-DCS source, and so on, up to an nth PLS-DCS source 12-n, 112-n. Aspects of the present disclosure described with respect to one PLS-DCS source 12, 112, 212, 312, 12-2, 112-2, . . . , 12-n, 112-n are applicable to any number of PLS-DCS sources 12, 112, 212, 312, 12-2, 112-2, . . . , 12-n, 112-n that are contained within the system 10, 110. A person having ordinary skill in the art will appreciate that the number of PLS-DCS sources is not intended to limited in this disclosure, and the number exemplified by the illustrated aspects are specific only for ease of explanation and brevity.

In certain aspects, the system 10, 110, 210, 310 can also optionally include a second reference optical path 30-2, 130-2, 230-2, 330-2 a third reference optical path, a fourth reference optical path, and so on, up to an nth reference optical path 30-n, 130-n, 230-n, 330-n.

In certain cases, the reference optical path can have a variable path length, so that the path length of the reference optical path can be adjusted and/or tuned to a preferred path length. The reference optical path 30, 130, 230, 330, 30-2, 130-2, 230-2, 330-2, . . . , 30-n, 130-n, 230-n, 330-n can include a path length controller (not illustrated), which enables control of the path length of the reference optical path 30, 130, 230, 330, 30-2, 130-2, 230-2, 330-2, . . . , 30-n, 130-n, 230-n, 330-n. In certain cases, the CPU 24, 124, 224, 324 can directly control the path length. In certain cases, an external controller can control the path length.

In certain cases, the reference optical path 30, 130, 230, 330, 30-2, 130-2, 230-2, 330-2, . . . , 30-n, 130-n, 230-n, 330-n can be an optical waveguide, such as an optical fiber, a free space optical path, or the like.

In certain aspects, the system 10, 110, 210, 310 can further optionally include other light sources beyond the PLS-DCS source 12, 112, 212, 312, which can collectively be referred to as additional light sources. These additional light sources can have similar properties to the PLS-DCS source 12, 112, 212, 312 or can have substantially different properties, and the different combinations and arrangements can have distinct advantages as described herein. In certain aspects, the additional light sources can be the sources listed with respect to the PLS-DCS source 12, 112, 212, 312 or can be a laser, a laser diode, an LED, a superluminescent diode, a broad area laser, a lamp, a white light source, and the like.

Referring to FIG. 2, a system 110 is illustrated that optionally includes multiple PLS-DCS sources 112, 112-2, . . . , 112-n and a single PLS-DCS detector 114.

Figure 3:
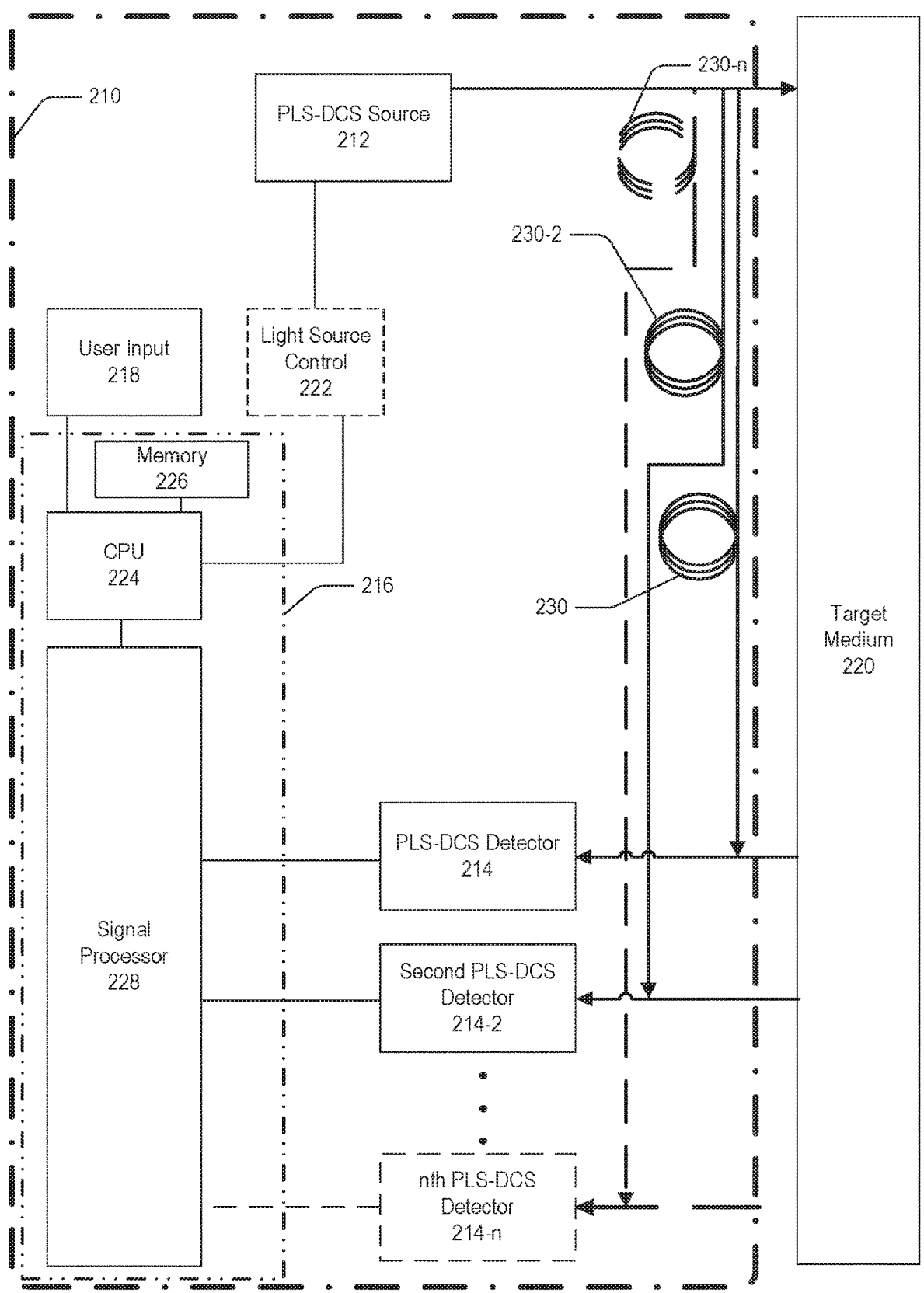
FIG. 3 is a schematic of a system, in accordance with the present disclosure.

Referring to FIG. 3, a system 210 is illustrated that includes a single PLS-DCS source 212, multiple PLS-DCS detectors 214, 214-2, . . . , 214-n, and multiple reference optical paths 230, 230-2, . . . , 230-n. In this illustrated aspect, the PLS-DCS source 212 emits light that is transmitted into the target medium 220 at a single location. Prior to entry into the target medium 220, the light emitted by the PLS-DCS source 212 has multiple portions split off for transmission along the multiple reference optical paths 230, 230-2, . . . , 230-n. The multiple PLS-DCS detectors 214, 214-2, . . . , 214-n are coupled to the target medium 220 at different locations, which in some cases can be at the same or different distances from the entry point of the light from the PLS-DCS source 212. Each PLS-DCS detector 214, 214-2, . . . , 214-n is paired with a reference optical path 230, 230-2, . . . , 230-n and those pairings function in the same fashion as described elsewhere herein. The path lengths of the reference optical paths 230, 230-2, . . . , 230-n can be selected based on the distances between the entry and exit points of the target medium 230 and the desired path length distribution of the resulting signal.

Figure 4:
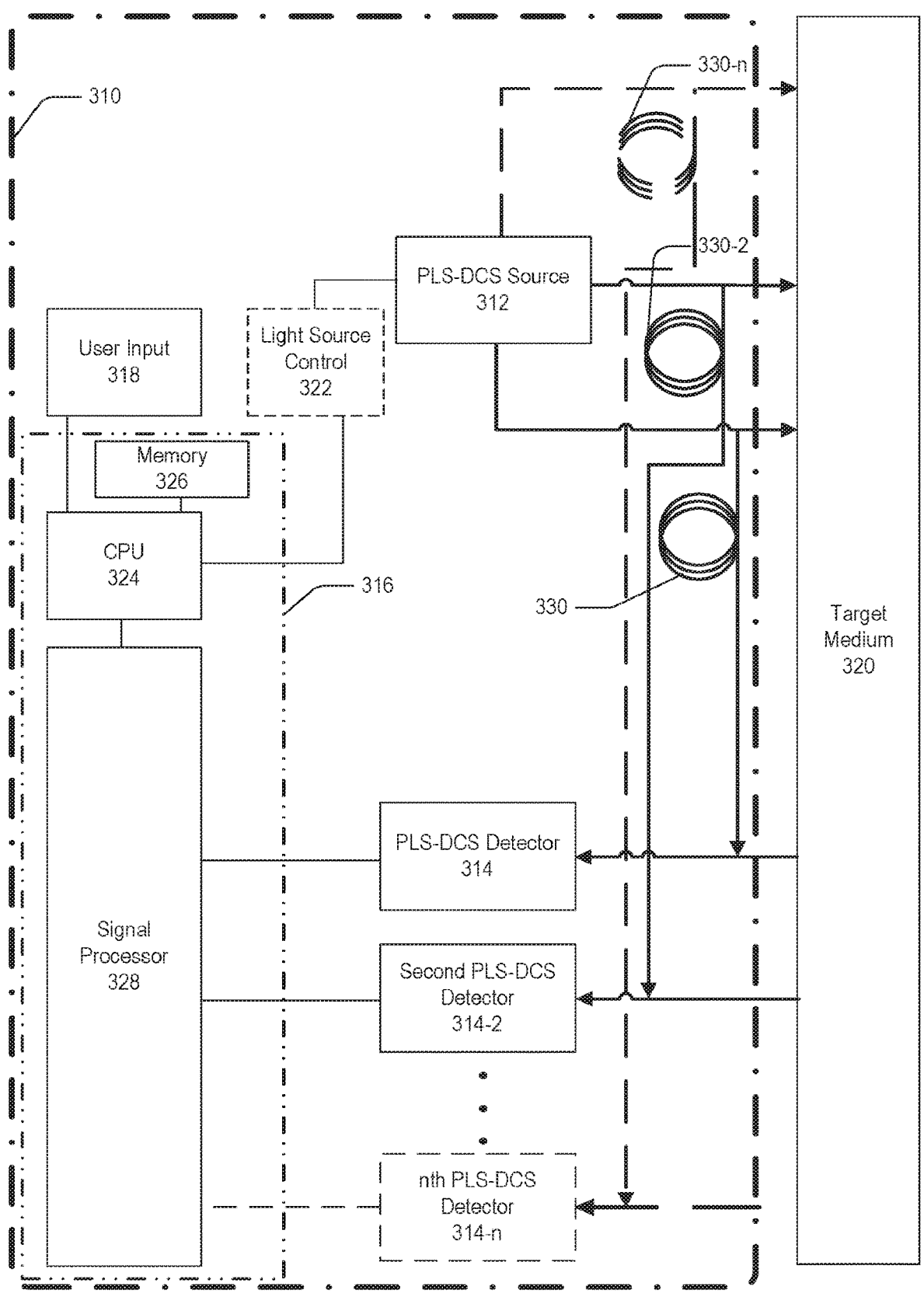
FIG. 4 is a schematic of a system, in accordance with the present disclosure.

Referring to FIG. 4, a system 310 is illustrated that includes a single PLS-DCS source 312, multiple PLS-DCS detectors 314, 314-2, . . . , 314-n, and multiple reference optical paths 330, 330-2, . . . , 330-n. In this illustrated aspect, the PLS-DCS source 312 emits light that is split into multiple portions and transmitted into the target medium 320 at multiple different locations. Prior to entry into the target medium, each of the multiple portions of the light has at least one additional portion split off for transmission along respective multiple reference optical paths 330, 330-2, . . . , 330-n. The function of the multiple PLS-DCS detectors 314, 314-2, . . . , 314-n and multiple reference optical paths 330, 330-2, . . . , 330-n utilize the same or similar principles as described above with respect to FIG. 3.

It should be appreciated that features shown and described with respect to system 10 are compatible and usable with systems 110, 210, 310, features shown and described with respect to system 110 are compatible and usable with systems 10, 210, 310, features shown and described with respect to system 210 are compatible and usable with systems 10, 110, 310, and features shown and described with respect to system 310 are compatible and usable with systems 10, 110, 210, unless the context clearly dictates otherwise. For example, the single detector arrangement of system 110 can be used with the single source arrangement of system 310.

For clarity, this disclosure explicitly contemplates any number of PLS-DCS sources 12, 112, 212, 312, 12-2, 112-2, . . . , 12-n, 112-n and PLS-DCS detectors 14, 114, 214, 314, 14-2, 214-2, 314-2 . . . , 14-n, 214-n, 314-n, up to 2, up to 5, up to 10, up to 25, up to 50, up to 100 or more, and up to n PLS-DCS sources 12, 112, 212, 312, 12-2, 112-2, . . . , 12-n, 112-n and/or PLS-DCS detectors 14, 114, 214, 314, 14-2, 214-2, 314-2, . . . , 14-n, 214-n, 314-n. In some cases, the number of PLS-DCS sources 12, 112, 212, 312, 12-2, 112-2, . . . , 12-n, 112-n is equal to the number of reference optical paths 30, 130, 230, 330, 30-2, 130-2, 230-2, 330-2, . . . , 30-n, 130-n, 230-n, 330-n. In some cases, the number of PLS-DCS sources 12, 112, 212, 312, 12-2, 112-2, . . . , 12-n, 112-n is equal to the number of PLS-DCS detectors 14, 114, 214, 314, 14-2, 214-2, 314-2, . . . , 14-n, 214-n, 314-n.

What follows is a non-limiting example of the use of the system 10, 110, 210, 310 illustrated in FIGS. 1, 2, 3, and 4. In this aspect, one or more laser sources produce light having a coherence length that is selected to be sensitive to a certain path length distribution within the target medium. The light is then split into two portions: a first portion which is directed onto a specimen and a second portion which is directed along a reference optical path. The length of the reference optical path is selected to be sensitive to the certain path length distribution within the target medium. The coherence length and the length of the reference optical path combine to determine which path lengths for which the technique is sensitive. The length of the reference optical path generally provides the mean path length for which the technique is sensitive and the coherence length generally provides the distribution around the mean path length. Light is received from the specimen (in other words, a part of the first portion of the light that is not absorbed or scattered by the specimen) via single-mode or multi-mode optical fibers. The received light is combined or multiplexed with the second portion of the light that was directed along the reference optical path. The combined or multiplexed light is then detected interferometrically.

The interfereometrically detected signals can be stored with a path length tag that identifies the path length for which signals are sensitive (in other words, the path length for which the coherence length and the length of the variable path length were selected). In this aspect, histograms of the path lengths are used to estimate $\mu_a$ and $\mu'_s$. In certain aspects, the correlation function and the decay rate slope can be used to calculate $\mu'_s$. These coefficients can be used to estimate flow, and optionally, hemoglobin concentrations and/or blood oxygenation, and result in improved accuracy, precision, and reduced variability with respect the prior art. The intensity correlation function is calculated from the arrival time tag. The correlation functions can be autocorrelation functions calculated from individual detectors, auto-correlation functions calculated from multiple detectors, cross-correlation functions calculated between different detectors, or any combination thereof. Photons are separated into one or more groups based on their time of flight. Different intensity correlations are calculated singly or in combination of one or more groups. The analysis of flow and other hemodynamic and metabolic values can be determined independently or through simultaneous global analysis of the path length tags from one or more sources and/or detectors. The results can provide a single average flow or can be divided to provide multiple flows. The results from different groups may represent flow values from different tissue depths. For example, results including all path lengths result in the conventional DCS result, results including groups of path lengths with shorter times of flight result in flows from more superficial tissues while groups with path lengths with longer times of flight result in flows from deeper tissues. This discrimination of signal by tissue depth has not been previously achieved.

In certain aspects, the PLS-DCS source 12, 112, 212, 312, the second PLS-DCS source 12, 112-2, the third, fourth, fifth, up to nth PLS-DCS Source 12-n, 112-n, or any additional light sources can include one or more amplifiers to amplify the intensity of the emitted light. In aspects including the amplifier, the source can be configured in a master oscillator power amplifier (MOPA) configuration.

In certain aspects, the amplifiers can change the properties of the light. For example, the PLS-DCS source 12 can include a laser having a coherence length that is longer or shorter than a desired coherence length, and the amplifier itself can be the source of the desired coherence length. For clarity, the PLS-DCS source 12 can be configured to emit light having certain properties described elsewhere herein, and those properties can originate from any of the components of the PLS-DCS source 12 including the PLS-DCS light source and/or the amplifier.

In certain aspects, the additional light sources can have properties that are substantially similar to those described with respect to the PLS-DCS source 12.

In certain aspects, the second PLS-DCS source 12, 112-2, the third, fourth, up to nth PLS-DCS source 12-n, 112-n, and/or additional PLS-DCS sources can have properties that are substantially similar to those described with respect to the PLS-DCS source 12, 112, 212, 312.

In some cases, the additional light sources or the additional PLS-DCS sources can be configured to emit light that is substantially similar to the light emitted from the PLS-DCS source 12, 112, 212, 312. In some cases, the additional light sources or the additional PLS-DCS sources can be configured to emit light that is suitable for PLS-DCS, but having one or more different properties than the PLS-DCS source. For example, the PLS-DCS source 12, 112 could emit light having a first coherence length and an additional light source or the second PLS-DCS source 12-2, 112-2 could emit light having a second, different, longer coherence length, which could allow the measurement of different properties. As another example, the PLS-DCS source 12, 112 could emit light having a first wavelength and the second PLS-DCS source 12-2, 112-2 could emit light having a second, different wavelength, which could allow the use of filters or multiplexing schemes to discriminate between signals originating from the respective sources. It should be appreciated that this discrimination can include optical, electronic, or optical and electronic discrimination.

Referring to FIGS. 1, 2, 3, and 4, the PLS-DCS sources 12, 112, 212, 312, 12-2, 112-2, . . . , 12-n, 112-n and additional light sources can be optionally controlled by a light source control 22, 122, 222, 322. The light source control 22, 122, 222, 322 can be configured to interface between the computer and the PLS-DCS sources 12, 112, 212, 312, 12-2, 112-2, . . . , 12-n, 112-n and additional light sources to provide control of the various operational parameters of the light sources described elsewhere herein. The light source control 22, 122, 222, 322 can control the coherence length of the light emitted from the various light sources.

In some cases, the light source control 22, 122, 222, 322 can be configured to control the sequence of the source for time division multiplexing between different sources. This control can be used with or without the control of coherence length described above.

In some cases, such as the case illustrated in FIG. 2 but also including other non-illustrated aspects, different sources can have reference optical paths to the same detector. In these cases, the light source control 22, 122, 222, 322 can select which source is active at a given time. In this fashion, a single detector can be used with different wavelength sources. IN this case, the reference optical paths can also be common between the various sources or there can be distinct reference optical paths for each source.

In certain aspects, the light source control 22, 122, 222, 322 can be a component of the computer 16, 116, 216, 316. In certain aspects, the light source control 22, 122, 222, 322 can be a standalone component or multiple standalone components. One light source control 22, 122, 222, 322 can control all or some of the various light sources or each of the various light sources can have its own light source control 22, 122, 222, 322.

The PLS-DCS detector 14, 114, 214, 314, 14-2, 214-2, 314-2 . . . , 14-n, 214-n, 314-n can be a light detector that is capable of detecting optical signals having the properties described elsewhere in the present disclosure. In some cases, the PLS-DCS detector 14, 114, 214, 314, 14-2, 214-2, 314-2 . . . , 14-n, 214-n, 314-n can be an interferometric detector. The PLS-DCS detector 14, 114, 214, 314, 14-2, 214-2, 314-2 . . . , 14-n, 214-n, 314-n can be an avalanche photodiode detector, such as a single-photon avalanche photodiode detector, a photomultiplier tube, a Si, Ge, InGaAs, PbS, PbSe, or HgCdTe photodiode or PIN photodiode, phototransistors, MSM photodetectors, CCD and CMOS detector arrays, silicon photomultipliers, multi-pixel-photon-counters, spectrometers, and the like. In certain aspects, the PLS-DCS detector 14, 114, 214, 314, 14-2, 214-2, 314-2 . . . , 14-n, 214-n, 314-n can be enhanced to be sensitive to a specific wavelength of light. In certain aspects, the PLS-DCS detector 14, 114, 214, 314, 14-2, 214-2, 314-2 . . . , 14-n, 214-n, 314-n can function as a monitor photodiode. In certain aspects, the PLS-DCS detector 14, 114, 214, 314, 14-2, 214-2, 314-2 . . . , 14-n, 214-n, 314-n can be a multi-pixel photo-detector that can be utilized to obtain many parallel detection channels on a single detector. In certain aspects including such a detector, a smaller pixel size can increase the DCS contrast. The PLS-DCS detector 14, 114, 214, 314, 14-2, 214-2, 314-2 . . . , 14-n, 214-n, 314-n can be analog or photon counting.

The PLS-DCS detector 14, 114, 214, 314, 14-2, 214-2, 314-2 . . . , 14-n, 214-n, 314-n can provide a detector signal that can be analog, digital, photon-counting, or any combination thereof.

Multiple PLS-DCS detectors can be used for selecting different depths of sensitivity using a single source-detector separation, by using different reference optical paths having different lengths. Multiple PLS-DCS detectors can be used with a single source, but with different source-detector separations.

In some cases, the PLS-DCS detectors can be used to combine PLS-DCS with different modalities, such as near-infrared spectroscopy.

In certain aspects, the system 10, 110, 210, 310 can further optionally include additional detectors that can be utilized for conducting other forms of spectroscopic measurements. These additional detectors can have similar properties to the PLS-DCS detector 14 or can have substantially different properties, and the different combinations and arrangements can have distinct advantages as described herein.

In certain aspects, the PLS-DCS detector 14, 114, 214, 314, or any additional detectors, the second PLS-DCS detector 14-2, 214-2, 314-2 the third, the fourth, fifth, up to nth PLS-DCS detector 14-n, 214-n, 314-n or any additional PLS-DCS detectors can be configured to receive optical signals from a single location or from multiple locations. Any combination of DCS detection can be achieved with the same or different detectors, including various combinations of detectors.

The system 10, 110, 210, 310 can optionally further include waveguides to couple the PLS-DCS source 12, 112, 212, 312, the PLS-DCS detector 14, 114, 214, 314, the additional light sources, and/or the additional detectors to the target medium 20, 120, 220, 320. The optional waveguides can be any waveguide suitable for delivering light having the properties described elsewhere herein. For example, the optical waveguides can be a fiber optic or a fiber optic bundle, a lens, a lens system, a hollow waveguide, a liquid waveguide, a photonic crystal, combinations thereof, and the like. It should be appreciated that the PLS-DCS source 12, 112, 212, 312 the PLS-DCS detector 14, 114, 214, 314, the additional light sources, and/or the additional detectors can be directly coupled to the target medium 20, 120, 220, 320.

In certain aspects, the waveguides can be deployed in a probe, including as many waveguides as is practical. In certain aspects, the probe can be affixable to a head of a subject. In certain aspects, the probe can be configured to provide multiple distinct source-detector distances. In certain aspects, the waveguides can be deployed in a catheter.

The various PLS-DCS detectors 14, 114, 14-2, 14-3, 14-$n$ or additional detectors can have intervening optics and/or pin hole(s), holograms, and/or detector active area dimensions. The various PLS-DCS detectors 14, 114, 14-2, 14-3, 14-$n$ or additional detectors can be used singly, multiply, arrayed, or in any combination.

In certain aspects, the PLS-DCS detectors 14, 114, 14-2, 14-3, 14-$n$ or additional detectors can have a small active area (i.e., 0.1 µm to 10 µm) to collect light from one or a few speckles, as can be required for DCS contrast, or can have a larger active area (i.e., 10 µm to 1 mm), which might not typically be associated with capabilities for DCS contrast. Combining different detectors with different performance for different modalities can have the advantage of improved overall performance and/or reduction in cost, weight, and/or power consumption. For example, the small active area required for DCS contrast can limit the maximum distance of the source-detector separation due to the decrease in transmission that is associated with a larger separation. On the other hand, time-resolved and continuous wave detection for non-DCS NIRS do not have this requirement, so detectors with different properties, including but not limited to a larger active area, a lower sensitivity, and the like, could be employed, using the same or different sources, or any combination of the above. Thus, a variety of source-detector separations can be utilized, thus enabling, for example, greater accuracy in determination of scattering and/or absorption coefficients than can be achieved using solely shorter separations. Some aspects have improved cost, weight, and/or power consumption. It should be appreciated that the specific aspects described are not intended to be limiting, and additional combinations of source or sources, detector or detectors, and distance or distances are possible.

The system 10, 110, 210, 310 can also include various other optics that a person having ordinary skill in the art would appreciate as being useful for aiding the acquisition of optical measurement. The system 10, 110, 210, 310 can include various lenses, filters, variable attenuators, polarizers, coupling optics, dielectric coatings, choppers (and corresponding lock-in amplification systems), pinholes, modulators, prisms, mirrors, fiber optic components (splitters/circulators/couplers), and the like.

In certain aspects, the PLS-DCS detector 14, 114, 214, 314, 14-2, 214-2, 314-2, . . . , 14-$n$, 214-$n$, 314-$n$ can be configured to receive optical signals from multiple different waveguides, where the multiple waveguides are a part of an optical path that includes a filter.

The computer 16, 116, 216, 316 can take the form of a general purpose computer, a tablet, a smart phone, or other computing devices that can be configured to control the measurement devices described herein, and which can execute a computer executable program that performs the simulations described herein. The computer 16 can include various components known to a person having ordinary skill in the art, such as a processor and/or a CPU 24, memory 26 of various types, interfaces, and the like. The computer 16 can be a single computing device or can be a plurality of computing devices operating in a coordinated fashion.

The computer 16, 116, 216, 316 can include a signal processor 28, 128, 228, 328 that is programmed to interpret the detected optical signals. For example, in some cases, the signal processor 28, 128, 228, 328 can be configured to calculate autocorrelation and/or cross correlation functions. In some cases, the signal processor 28, 128, 228, 328 can be configured to store photon arrival times and forward the arrival times for correlation procession. In some cases, the signal processor 28, 128, 228, 328 can be configured to apply a correlation-diffusion equation. As non-limiting examples, the signal processor 28, 128, 228, 328 can be implemented as a field-programmable gate array (FGPA), an application-specific integrated circuit (ASIC), a system on a chip (SOC), a microprocessor, a microcontroller, or the like.

In certain aspects, the signal processor 28, 128, 228, 328 can be configured to extract measurement from the photon signals by a variety of means, including but not limited to, Fourier or other transform methods, heterodyning or homodyning methods, or a combination thereof, with examples including but not limited to, hardware-based extraction, software-based extraction, linear transforms, log transforms, multitau correlation, and combinations thereof.

A detector signal from one of the detectors can be multiplexed to individual processing paths, such as those discussed below, to be processed for DCS measurements. This multiplexing can afford efficiency in the processing.

The processor and/or CPU 24, 124, 224, 324 can be configured to read and perform computer-executable instructions stored in the memory 26, 126, 226, 326. The computer-executable instructions can include all or portions of the methods described herein.

The memory 26, 126, 226, 326 can include one or more computer readable and/or writable media, and may include, for example, a magnetic disc (e.g., a hard disk), an optical disc (e.g., a DVD, a Blu-ray, a CD), a magneto-optical disk, semiconductor memory (e.g., a non-volatile memory card, flash memory, a solid state drive, SRAM, DRAM), an EPROM, an EEPROM, and the like. The memory can store the computer-executable instructions for all or portions of the methods described herein.

The user interface 18, 118, 218, 318 can provide communication interfaces to input and output devices, which can include a keyboard, a display, a mouse, a printing device, a touch screen, a light pen, an optical storage device, a scanner, a microphone, a camera, a drive, a communication cable, or a network (wired or wireless). The interfaces can also provide communications interfaces to the PLS-DCS source 12, 112, 212, 312, the PLS-DCS detector 14, 114, 214, 314, and other sources and/or detectors includes in the system 10, 110, 210, 310 and/or used in the methods described herein.

The PLS-DCS source 12, 112, 212, 312 and the PLS-DCS detector 14, 114, 214, 314 can be controlled by the computer 16, 116, 216, 316. The computer 16, 116, 216, 316 can have stored on it a computer executable program configured to execute such control. The computer 16, 116, 216, 316 can direct the PLS-DCS source 12, 112, 212, 312 to emit optical signals that are configured to enter into the layered target medium in a fashion that allows the optical signals to interact with fluid flow in the target medium 20, 120, 220, 320, including an inner region of the target medium 20, 120, 220, 320. This interaction can allow the optical signals to acquire information related to the fluid flow in the inner region. The computer 16, 116, 216, 316 can direct the PLS-DCS detector 14, 114, 214, 314 to detect the optical signals that contain the acquired information.

In certain aspects, the system 10, 110, 210, 310 can include an imaging modality or a layer thickness measuring modality for characterizing the target medium 20, 120, 220, 320 and providing additional useful information. Examples of suitable imaging and/or layer thickness measuring modalities can include, but are not limited to, an ultrasound imaging system, a non-imaging ultrasound system configured to transmit and receive a reflected acoustic wave, an MRI imaging system, an x-ray imaging system, a computed tomography imaging system, a diffuse optical tomography imaging system, an optical layer thickness measurement system, combinations thereof, or the like. In other aspects, an ultrasound system could be configured to transmit an acoustic wave for depth-specific modulation of the light. Detecting this modulation in the PLS-DCS signal could further aid depth discrimination of the flow and hemoglobin information.

In some aspects, the PLS-DCS source 12, 112, 212, 312, the PLS-DCS detector 14, 114, 214, 314, the computer 16, 116, 216, 316 of the system 10, 110, 210, 310 and other components of the system 10, 110, 210, 310 described herein, including additional PLS-DCS sources and/or additional PLS-DCS detectors, can be contained in a single unit that is portable and suitable for point-of-care use. In some aspects, the single unit can be handheld. In some aspects, the computer 16, 116, 216, 316 can be a handheld computing device and the remainder of the system 10, 110, 210, 310 can be contained in a single unit that is portable and/or handheld. In some aspects, the system 10, 110, 210, 310 can be contained in one or more handheld units. In some aspects, the system 10, 110, 210, 310 or various components of the system 10, 110, 210, 310 can be contained in a wearable device.

In some aspects, the PLS-DCS source 12, 112, 212, 312, the PLS-DCS detector 14, 114, 214, 314, and the computer 16, 116, 216, 316 of the system 10, 110, 210, 310 and other components of the system 10, 110, 210, 310 described herein, including additional PLS-DCS sources and/or additional PLS-DCS detectors, can be contained in a table-top unit that is suitable for placement on a table-top and can be located appropriately for point-of-care use.

The system 10, 110, 210, 310 can be powered by a power supply that is supplied electricity from a wall outlet or via one or more batteries, either rechargeable or replaceable.

It should be appreciated that various aspects of the system 10, 110, 210, 310 that are illustrated as blocks are shown in this fashion for illustrative purposes, and those blocks can be multiple separate elements or can be combined into single monolithic elements.

One advantage of the system 10, 110, 210, 310 is that both deep and superficial flows can be captured using the same detector, with a single source-detector separation. A reduction in the necessary number of detectors can provide improvements with respect to cost, size, weight, and complexity. It should be appreciated, however, that a second separation detector can be utilized in combination with these features. In these cases, the path length selection in concert with the second source-detector separations can improve detection of the signal of interest relative to the use of one separation detector alone. It should also be appreciated that multiple separation detectors can be utilized, with the different path length distributions in concert with the multiple source-detector separations improving detection of the signal of interest relative to the use of one source-detector separation alone.

Another advantage of the system 10, 110, 210, 310 is that very small, lightweight detector fibers or solid state detectors can be used, and thus bendable probes can be used. In some aspects, the PLS-DCS system 10, 110, 210, 310 can utilize the same small fibers or the same solid state components as a source and a detector, thereby reducing the number of fibers or electrical components required in a probe. Smaller probes can be desirable for vulnerable patients, such as infants, placement around surgical and/or wound sites, and for use with other measurement modalities, such as EEG, cranial bolts, and the like. Smaller probes are also advantageous for implantable, chronic, mobile, and/or wearable applications. Additional advantages can include reduced cost, weight, and/or power consumption.

Aspects of the present disclosure discussed below with respect to the methods 300, 400 are applicable to and can be incorporated in the systems 10, 110, 210, 310 described herein. For clarity, if the methods below describe an aspect that a person having ordinary skill in the art would understand as implying the presence of structural features in the systems 10, 110, 210, 310 described above, then this disclosure expressly contemplates the inclusion of those structural features. As a non-limiting example, if the methods below describe focusing light, then a person having ordinary skill in the art would understand that this implies the presence of a focusing lens or a structure that serves the purpose of a focusing lens, such as a concave curved mirror.

Methods

This disclosure provides methods 400, 500 for using the systems 10, 110, 210, 310 described above, although the methods 400, 500 can optionally be used with other systems not described herein.

Figure 6:
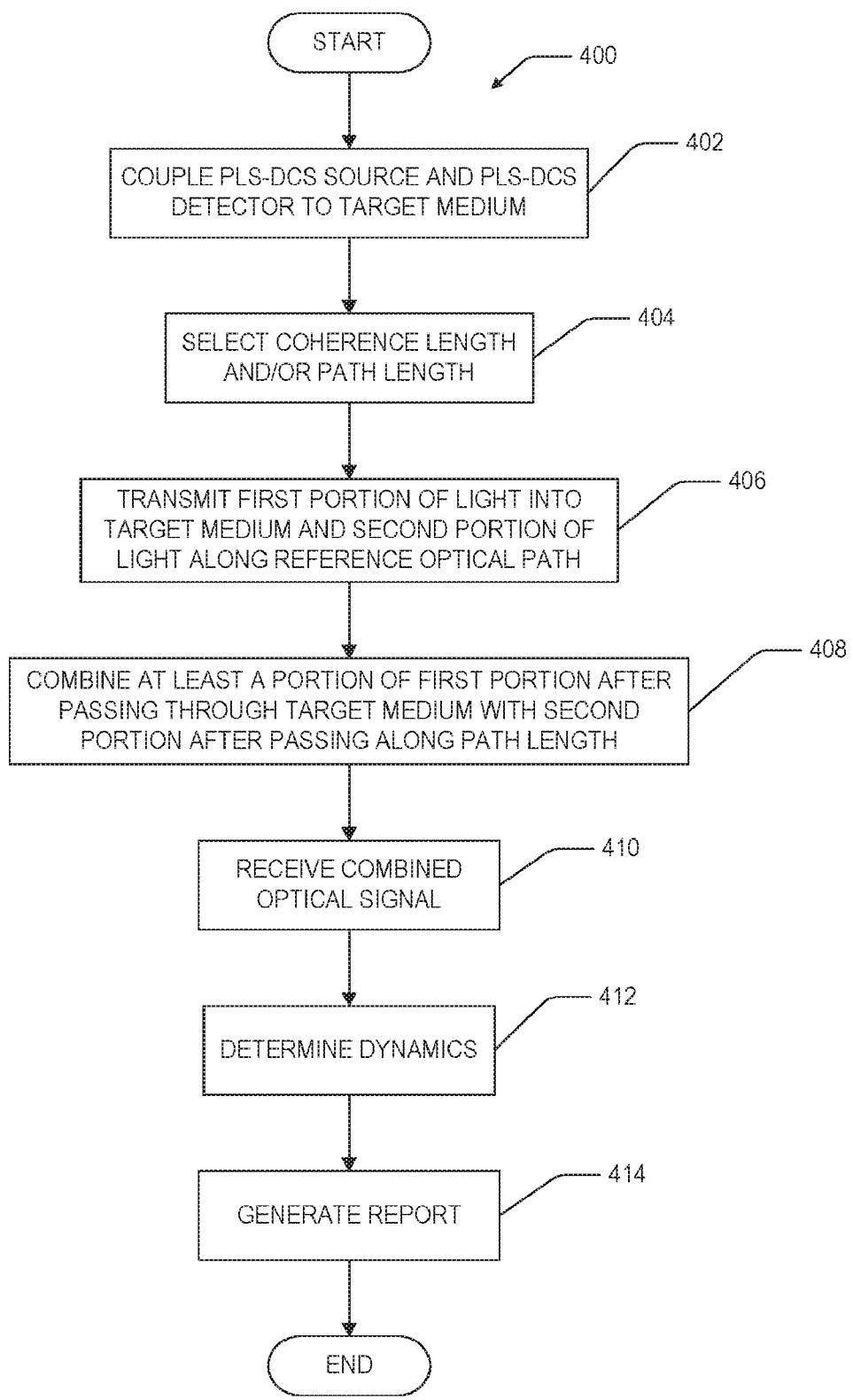
FIG. 6 is a flowchart of a method, in accordance with the present disclosure.

Referring to FIG. 6, the present disclosure provides a method 400 for making a PLS-DCS measurement of scattering particle dynamics within a target medium. At process block 402, the method 400 includes coupling a PLS-DCS source and a PLS-DCS detector to the target medium. The PLS-DCS source is configured to emit a first light having a first coherence length of less than a path length distribution of the target medium. At process block 404, the method 400 includes selecting the first coherence length of the first light and/or a first path length of a first reference optical path to acquire a PLS-DCS measurement for a desired path length distribution of the target medium. At process block 406, the method 400 includes transmitting a first portion the first light from the PLS-DCS source into the target medium and a second portion of the first light along the first reference optical path. At process block 408, the method 400 includes combining at least a portion of the first portion of the first light after passing through the target medium and the second portion of the first light after passing along the first path length of the first reference optical path, thereby providing a combined optical signal. At process block 410, the method 400 includes receiving the combined optical signal at the PLS-DCS detector, thereby generating a PLS-DCS detector signal including path length information and correlation information for the combined optical signal. At process block 412, the method 400 includes determining, using a processor, the path length information, the correlation information, and one or more equations relating path length and correlation to dynamics, a dynamics of the target medium. At process block 414, the method 400 includes generating a report including the dynamics of the target medium.

In some cases, process block 404 can include selecting the coherence length. In some cases, process block 404 can include selecting the path length.

In some cases, process blocks 402, 404, and 406 can be repeated with different distances between the PLS-DCS source and the PLS_DCS detector. In these cases, the determining of process block 412 can utilize the different distances. In these cases, the determining of process block 412 can compensate for the differences in the path length information due to the different distances.

Figure 7:
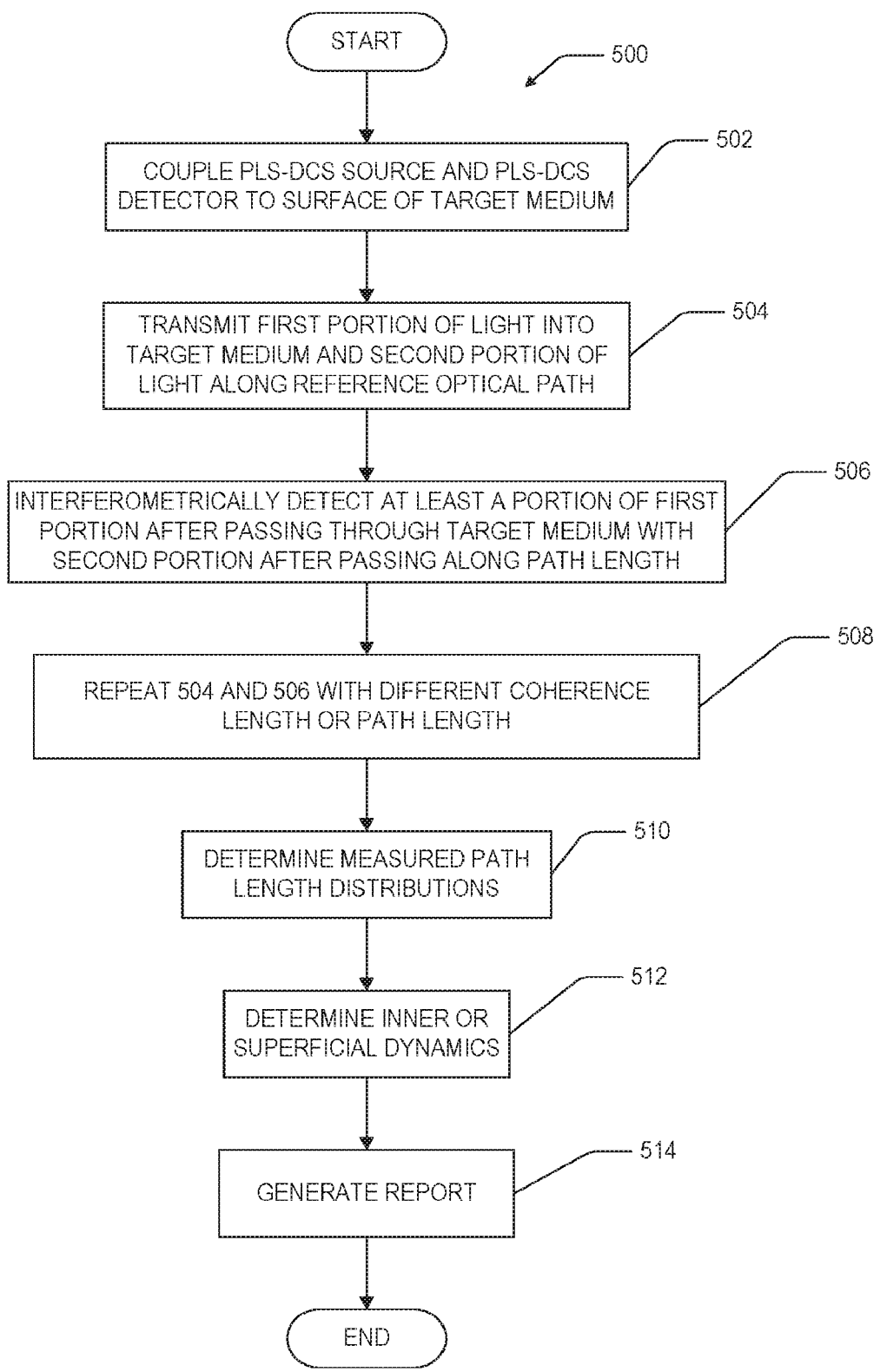
FIG. 7 is a flowchart of a method, in accordance with the present disclosure.

Referring to FIG. 7, the present disclosure provides a method 500 of making a PLS-DCS measurement of a target medium. At process block 502, the method 500 includes coupling a PLS-DCS source and a PLS-DCS detector to a surface of the target medium. At process block 504, the method 500 includes transmitting a first portion of a first light from the PLS-DCS source into the target medium and a second portion of the first light along a reference optical path, the first light having a first coherence length of less than a path length distribution of the target medium. At process block 506, the method 500 includes interferometically detecting, using the PLS-DCS detector, at least a portion of the first portion of the first light after passing through the medium and the second portion of the first light after passing along a first path length of the reference optical path, thereby generating a first interferometric signal. At process block 508, the method 500 includes repeating process blocks 504 and 506, substituting a second coherence length for the first coherence length and a second path length for the first path length, thereby generating a second interferometric signal in place of the first interferometric signal, wherein the second coherence length is different than the first coherence length or the second path length is different than the first path length. At process block 510, the method 500 includes determining a first measured path length distribution based on the first coherence length and the first path length and a second measured path length distribution based on the second coherence length and the second path length. At process block 512, the method 500 includes determining, using a longer distribution between the first measured path length distribution and the second measured path length distribution, an inner dynamics of an inner portion of the target medium relative to the surface, or, using a shorter distribution between the first measured path length distribution and the second measured path length distribution, a superficial dynamics of a superficial layer of the target medium relative to the surface. At process block 514, the method 500 includes generating a report including the inner dynamics or the superficial dynamics.

In some cases, process blocks 502, 504, 506, and 508 can be repeated with different distances between the PLS-DCS source and the PLS_DCS detector. In these cases, the determining of process block 510 can utilize the different distances.

It should be appreciated that more than two wavelengths of light can be used in the methods 400, 500, and that dynamics and properties can be determined for a corresponding more than two species. Determining the dynamics for a particular number of species can involve use of at least the same number of wavelengths. A person of ordinary skill in the art would appreciate how to solve what can be essentially a linear mixing problem using tools known in the art.

The methods 400, 500 can optionally further include determining a fluid flow in the target medium. The fluid flow can be determined for each of the first species and second species, or any additional species.

In certain aspects, the first species can be oxyhemoglobin and the second species can be deoxyhemoglobin. The methods 400, 500 can optionally further include determining a hemoglobin, oxyhemoglobin, and/or deoxyhemoglobin concentration, a hemoglobin oxygen saturation and/or a metabolic rate of oxygen. The determining can use the dynamics and/or the fluid flow. The report generated at process blocks 414, 514 can optionally include the fluid flow, the hemoglobin oxygen dynamics, and/or the metabolic rate of oxygen, either with or in place of the dynamics.

The determining of process blocks 412, 512 can include calculating using one or more of the equations or concepts described herein. The determining of process blocks 412, 512 can include fitting data in ways known to those having ordinary skill in the art. The determining of process blocks 412, 512 can be executed on a processor or CPU 24, 124, 224, 324.

The generating a report of process blocks 414, 514 can include generating a printed report, displaying results on a screen, transmitting results to a computer database, or another means of reporting the mathematically modeled fluid flow, as would be apparent to a person having ordinary skill in the art. The method is not intended to be limited to a specific report generation.

In certain aspects, the dynamics that are determined by the methods described herein can be fluid flow, shear flow, diffusional properties, motion, association, dis-association, aggregation, dis-aggregation, and/or rotational dynamics of the optical scattering particles within the target medium, and the like.

In certain aspects, dynamics and/or fluid flow can be determined from by calculating the correlation function from the path length distribution for the given coherence length of the light and/or path length of the reference optical path. Other aspects can utilize other means of measuring dynamics and/or fluid flow, including but not limited to, power spectrum analysis, moment analysis, and the like. The analysis can be performed singly, and/or independently or globally across multiple groups, or combinations thereof. The analysis can be performed by components of the system 10, 110, 210, 310 described above that a person having ordinary skill in the art would appreciate as being capable of the analysis.

In certain aspects, the methods described herein can utilize measurement at two, three, four, five, six, or more, up to n source-detector distances. Use of multiple source-detector distances can provide better discrimination between various different depths of measurement, such as between cerebral and extra-cerebral measurements. When using multiple source-detector distances, the determinations of the methods can compensate for differences in the path length distributions that result from the different source-detector distances.

In certain aspects, the methods described herein can utilize two or more different wavelengths of light. Use of two or more different wavelengths of light can afford determination of dynamics for two or more different species. The two or more different wavelengths can afford better quantification of flow, absorption and scattering coefficient measurements, and quantification of hemoglobin concentrations and/or hemoglobin oxygen saturation, which in combination with cerebral blood flow, can provide a measure of $CMRO_2$. Global analysis can be used to simultaneously determine the flow and hemoglobin concentrations and/or oxygen saturation.

In certain aspect, the methods described herein can combine PLS-DCS with CW and time-domain or frequency-domain NIRS.

In certain aspects, the methods described herein can measure properties of the target medium 20, 120, 220, 320 in a baseline state, in a state of spontaneous change, in an evoked change, or a combination thereof. Comparing the measurement of a property following an evoked change with a measurement at a baseline state can provide information regarding the evoked change.

In certain aspects, the methods described herein can utilize detected signals from a single site or multiple sites.

In certain aspects, the correlation described herein can be normalized or unnormalized.

In certain aspects, only a portion of the overall path length distribution can be analyzed. For example, when measuring properties of a deeper portion of the target medium 20, 120, 220, 320, only the later portion of the path length distribution may be analyzed. As another example, many small portions of the path length distribution (consecutive or partially overlapping) can be analyzed.

In certain aspects, the methods described herein can measure the optical properties of the target medium 20, 120, 220, 320 at the same wavelength and in the same location. The measured properties can be used to reduce intra- and inter-subject variability due to anatomy and physiology.

Calculations, separation, and/or discrimination in the methods described herein can be performed in real-time, near real-time, post-processing, or a combination thereof. These operations can be performed continuously, quasi-continuously, and/or continually, or periodically, and/or intermittently or in batches, or any combination thereof. Alerts, alarms, and/or reports can be generated in response to the results. The alerts, alarms, reports, and/or results can be displayed locally and/or remotely transmitted.

In certain aspects, the methods described herein, and in particular, the path length selecting features thereof, can be utilized to acquire measurements that are sensitive to areas of the target medium 20, 120, 220, 320 that are near the surface, and can be achieved with a greater source-detector separation, whereas previous methods required a short source-detector separation to isolate measurements near the surface. Similarly, the methods described herein, and in particular, the path length selecting features thereof, can be utilized to acquire measurements that are sensitive to areas of the target medium 20, 120, 220, 320 that are deeper, and can be achieved with a shorter source-detector separation, whereas previous methods required a long source-detector separation to isolate measurements deeper in the target medium 20, 120, 220, 320. One advantage that a short source-detector separation provides is that a larger number of photons can be measured, thereby improving the signal-to-noise ratio.

The target medium 20, 120, 220, 320 can include an inner region and a superficial layer. The superficial layer can include one, two, three, four, five, six, or more distinct layers. In some aspects, the superficial layer can include two, three, or four distinct layers.

The superficial layer can include a skull of a subject, a scalp of a subject, a fluid layer between the skull and a cerebral region of a subject, or a combination thereof. The inner region can include a cerebral region of a subject.

The fluid can be blood, water, cerebro spinal fluid (CSF), lymph, urine, and the like. The fluid flow can be blood flow, water flow, CSF flow, lymph flow, urine flow, and the like.

In certain aspects, the target medium 20, 120, 220, 320 can be an industrial fluid of interest. In certain aspects, the target medium 20, 120, 220, 320 can be tissue, including but not limited to, mammalian tissue, avian tissue, fish tissue, reptile tissue, amphibian tissue, and the like. In certain aspects, the target medium 20, 120, 220, 320 can be human tissue.

Aspects of the present disclosure discussed above with respect to the systems 10, 110, 210, 310 are applicable to and can be incorporated in the methods described herein. For clarity, if the systems above describe a structural feature that a person having ordinary skill in the art would understand as implying the presence of a method step or feature in the methods described above, then this disclosure expressly contemplates the inclusion of those method steps or features. As a non-limiting example, if the methods above describe a focusing lens that receives a collimated light beam, then a person having ordinary skill in the art would understand that this implies the presence of a method step or feature involving focusing of light.

Computational Considerations

The decay of the intensity correlation function can be described by a correlation diffusion equation that is similar to the regular photon diffusion equation but replacing the traditional absorption coefficient ($\mu_a$) with a dynamic absorption coefficient. That is, in the traditional photon diffusion equation, $\mu_a$ is replaced with the dynamic absorption term $\mu_a + 2\mu'_s D_B k_o^2 \tau$ to obtain the correlation diffusion equation, where $\mu'_s$ is the reduced scattering coefficient, $D_B$ is the Brownian diffusion coefficient acting as an index of blood flow, $k_o = 2\pi n/\lambda$ is the wavenumber of light, and $\tau$ is the correlation time. Thus, the solution of the time domain-diffuse correlation diffusion equation can be obtained from the traditional TD-NIRS solution by making this replacement. For a semi-infinite medium, the time-domain DCS (TD-DCS) solution for the field auto-correlation function, $G_1$, is thus:

$$G_1(\tau, \rho, z=0, t) = 2\pi c z_b (z_0 + 2z_b) \left(\frac{3\mu'_s}{4\pi c t}\right)^{\frac{5}{2}} \exp\left(-(\mu_a + 2\mu'_s D_B k_o^2 \tau) c t\right) \exp\left(-\frac{3\mu'_s \rho^2}{4 c t}\right), \quad (1)$$

where t is the arrival time of the photons with respect to the laser pulse at t=0, $\rho$ is the source-detector separation.

The normalized field temporal auto-correlation function is obtained by dividing $G_1(\tau)$ by $G_1(\tau=0)$. Doing so, the path length dependent auto-correlation function is obtained, as follows:

$$g_{1s}(\tau,S) = \exp(-2\mu'_s D_B k_o^2 S \tau), \quad (2)$$

where the transit time of flight through the tissue, t, has been replaced with the path length of light through the tissue, S. This is an important equation as it indicates that the decay rate of the field temporal auto-correlation function increases linearly with the photon path length. Another important result of this equation, is that the path length dependent decay of $g_{1s}(\tau,S)$ is independent of the absorption coefficient of the medium $g_{1s}(\tau,S)$ was originally derived by first principles and extended to CW-DCS with a long coherence source by integrating over the distribution of detected photon path lengths, i.e.

$$g_1(\tau) = \int ds\, P(s) g_{1s}(\tau,s) \quad (3)$$

For light diffusion through a highly scattering medium, P(s) is given by the solution of the time-domain photon diffusion equation.

Experimentally, the normalized intensity auto-correlation function ($g_2$) is measured, which is related to $G_1$ by $g_2 = 1 + \beta G_1^2(\tau)/G_1^2(\tau=0)$, where $\beta$ accounts for loss of coherence due to the spatial and temporal coherence of the detected light. For PLS-DCS, the coherence length of the pulse of light is less than the distribution of photon path lengths through the scattering medium, so $g_2$ is determined by the relation:

$$g_2(\tau) = 1 + \int ds \int ds'\, g_1(s, \tau) g_1(s', \tau) e^{-2\left[\frac{(s-s')}{l_c}\right]^2} \quad (4)$$

where $l_c$ is the coherence length of the PLS-DCS source. The Gaussian function in the integrand limits the contribution of the path length dependent autocorrelation function within an envelope where the difference in path lengths is comparable to the coherence length. In this sense, the coherence of the source acts as an intrinsic tag of the path length the photons took to reach the detector. The photons were instantaneously coherent at the source for a period of time given by the coherence time of the source. Photons for which the difference in the time of flight is greater than this period will not coherently add to the correlation function. Interferometric detection selects contributions to $g_2$ localized to paths with differences within this envelope around the length of the reference arm. A lower coherence source will provide greater path length resolution at a cost of a smaller β value. DCS signal-to-noise ratio (SNR) is linearly proportional to β. Spatial coherence, and by extension (SNR), is maximized by limiting the detected area, typically by using a single mode fiber to define the detection. The best values of β achieved in conventional DCS is 1 using polarizers or 0.5, without polarizers.

The drop in SNR can be overcome, for example, by detecting more photons than acquired in CW-DCS. This increase is practical to achieve by simply using shorter separations, greater laser powers, or longer integration times. Thus, by using lower coherence source, DCS SNR marginally decreases, but this decrease is unexpectedly offset by the benefits of the aspects of this disclosure, thus producing an unanticipated net increase in performance.

For both DCS and non-DCS spectroscopy modalities, measurements at multiple distances facilitate the discrimination of cerebral parameters from the confounding effects of the scalp. For example, by measuring NIRS at multiple different distances, intracerebral signals can be separated from extra-cerebral ones. These aspects also enable novel strategies for PLS-DCS, alone or in conjugation with other modalities, especially including multi-layer fitting to quantify cerebral and extra-cerebral optical properties and blood flow. Thus, this disclosure is a significant innovation which directly addresses the most fundamental complications of transcutaneous cerebral optical measurements. The measurements and analyses of this disclosure can be performed with a single source-detector separation, or across multiple distances with multiple detector and/or sources with global or independent analysis, in any combination, in whole or in part.

We claim:

1. A method for making a path length selected diffuse correlation spectroscopy (PLS-DCS) measurement of scattering particle dynamics within a target medium, the method comprising:
   a) coupling a PLS-DCS source and a PLS-DCS detector to the target medium, the PLS-DCS source configured to emit a first light having a first coherence length of less than a path length distribution of the target medium;
   b) selecting the first coherence length of the first light and/or a first path length of a first reference optical path to acquire a PLS-DCS measurement for a desired path length distribution of the target medium;
   c) transmitting a first portion the first light from the PLS-DCS source into the target medium and a second portion of the first light along the first reference optical path;
   d) combining at least a portion of the first portion of the first light after passing through the target medium and the second portion of the first light after passing along the first path length of the first reference optical path, thereby providing a combined optical signal;
   e) receiving the combined optical signal at the PLS-DCS detector, thereby generating a PLS-DCS detector signal including path length information and correlation information for the combined optical signal;
   f) determining, using a processor, the path length information, the correlation information, and one or more equations relating path length and correlation to dynamics, a dynamics of the target medium; and
   g) generating a report including the dynamics of the target medium.

2. The method of claim 1, wherein the determining of step d) includes determining at two or more different desired path length distributions, thereby providing depth-dependent information about the dynamics of the target medium.

3. The method of claim 1, wherein the PLS-DCS detector signal thereby generated by the receiving of step e) includes wavelength information, and the determining of step f) uses the wavelength information.

4. The method of claim 1, wherein steps a), b), and c), are repeated with a different distance between the PLS-DCS source and the PLS-DCS detector.

5. The method of claim 1, wherein the determining of step f) includes fitting data.

6. The method of claim 1, the method further comprising:
   a1) coupling a second PLS-DCS source and optionally a second PLS-DCS detector to the target medium, the second PLS-DCS source configured to emit a second light having a second coherence length of less than the path length distribution of the target medium;
   b1) selecting the second coherence length of the second light and/or a second path length of a second reference optical path to acquire a PLS-DCS measurement for a second desired path length distribution of the target medium;
   c1) transmitting a third portion of the second light from the second PLS-DCS source into the target medium and a fourth portion of the second light along the second reference optical path;
   d1) combining at least a portion of the third portion of the second light after passing through the target medium and the fourth portion of the second light after passing along the second path length of the second reference optical path, thereby providing a second combined optical signal;
   e1) receiving the second combined optical signal at the PLS-DCS detector or the second PLS-DCS detector, thereby generating a second PLS-DCS detector signal including second path length information and second correlation information for the second combined optical signal,
   the determining of step f) using the second timing information and the second correlation information.

7. The method of claim 1, wherein the dynamics of the target medium include a fluid flow within the target medium.

* * * * *